United States Patent [19]

Horstmann et al.

[11] Patent Number: 5,932,239
[45] Date of Patent: Aug. 3, 1999

[54] TRANSDERMAL THERAPEUTIC SYSTEM WITH PROTECTION AGAINST HYDROLYSIS

[75] Inventors: Michael Horstmann; Hanshermann Franke, both of Neuwied, Germany

[73] Assignee: LTS Lohmann Therapie-Systeme GmbH, Neuwied, Germany

[21] Appl. No.: 08/793,724

[22] PCT Filed: Aug. 12, 1995

[86] PCT No.: PCT/EP95/03204

§ 371 Date: Jun. 12, 1997

§ 102(e) Date: Jun. 12, 1997

[87] PCT Pub. No.: WO96/06600

PCT Pub. Date: Mar. 7, 1996

[30] Foreign Application Priority Data

Aug. 20, 1994 [DE] Germany .............................. 44 29 663

[51] Int. Cl.$^6$ ...................................... A61F 13/02

[52] U.S. Cl. ............................................ 424/449; 424/448
[58] Field of Search ...................................... 424/448, 449

[56] References Cited

U.S. PATENT DOCUMENTS

| | | | |
|---|---|---|---|
| 4,409,206 | 10/1983 | Stricker | 424/81 |
| 4,756,710 | 7/1988 | Bondi | 424/449 |
| 5,362,497 | 11/1994 | Yamada | 424/449 |
| 5,429,590 | 7/1995 | Saito | 602/48 |

*Primary Examiner*—D. Gabrielle Brouillette
*Attorney, Agent, or Firm*—Wenderoth, Lind & Ponack, L.L.P.

[57] ABSTRACT

A transdermal therapeutic system (TTS) comprising an active substance which is sensitive to hydrolysis, and having a layer-like structure comprising a backing layer impermeable to moisture and active substance, a matrix comprising the active substance, and optionally a protective layer covering the matrix is characterized in that the matrix contains a water-binding component.

20 Claims, No Drawings

TRANSDERMAL THERAPEUTIC SYSTEM WITH PROTECTION AGAINST HYDROLYSIS

This application is a 371 of PCT/EP95/03204, filed Aug. 12, 1995.

BACKGROUND OF THE INVENTION

In the galenic conversion of a pharmaceutical into a drug form, the stabilization of pharmaceuticals or adjuvants that are sensitive to hydrolysis is a matter of widespread concern. In the following, the term "hydrolysis" is understood to mean the cleavage of a substance through the effect of water. This applies, in particular, to the hydrolytic cleavage of esters, acetals, ketals, animals, and the hydrolytic cleavage of peptide pharmaceuticals.

Generally, protection against hydrolysis can be achieved by the following methods:

1. Adjusting a particular pH value, which—according to experimental findings—results in the lowest possible rate constant for the degradation of the component (1) which is sensitive to hydrolysis.

2. Forming complex bounds of the active component which is sensitive to hydrolysis by addition of suitable reactants (2) capable of complex formation. This leads to stabilisation in all those cases where the hydrolytic degradation takes place exclusively in the hydrolysis-sensitive component which is not present as a complex.

3. Decreasing the solubility of the hydrolysis-sensitive component in a medium by controlled addition of suitable substances (3, 4). Examples for this are the pH adjustment by buffer solutions and the formation of insoluble derivatives that have no propensity for solvolysis.

4. Removing water from the drug form or maintaining as far as possible an almost water-free environment of the hydrolysis-sensitive active component in a drug form (5).

All of the above-mentioned approaches 1–4 are of great importance in the pharmaceutics industry and are more or less common, depending on the form of drug. Most of these are only partially suitable for the transdermal application of pharmaceuticals by so-called transdermal therapeutic systems. The transdermal availability of a pharmaceutical is first of all dependent on its physicochemical properties. Mostly, these are negatively affected by pH changes, complexation, and by derivatisation, which is why the above-mentioned methods 1–3 are suitable only in certain cases.

The safest method is therefore to keep the active ingredient which is embedded (dissolved or dispersed) in a transdermal therapeutic system in a largely water-free environment.

The prior art known in respect of this topic can be described by two methodical approaches:

a) The production of single-dose drugs comprising a hydrolysis-sensitive pharmaceutical or adjuvant takes place under exclusion of moisture (water or water vapour) and employing primary and secondary means of packaging or packages which represent a migration barrier for the moisture present in the environment during storage and which thereby maintain the interior of the package containing the hydrolysis-sensitive component largely water-free.

b) The use of water-binding substances within the secondary package in order to bind the moisture entering the package during storage and thereby to minimise the moisture content within the primary package.

c) The use of water-binding substances within the primary package, for example by water-binding drying agents integrated in the lid of the vessel.

By contrast to most other drug forms, in transdermal therapeutic systems the primary package has an extremely large surface area. Furthermore, patch-like transdermal therapeutic systems cannot be bent or folded to keep the surface area of the package as small as possible. Thus, in such systems the primary package provides a correspondingly large boundary surface for the migration of moisture into the package. For this reason, methods a) to c) are not always sufficient to ensure the required maximum moisture content even over prolonged periods of time and under all kinds of storage conditions, and to stabilise the hydrolysis-sensitive ingredient.

SUMMARY OF THE INVENTION

It is the object of the present invention to stabilize transdermal therapeutic systems comprising a hydrolysis-sensitive active component preventing the intrusion of moisture into the single-dose drug form by using a suitable packaging material, and that moisture which has nevertheless entered the primary package does not lead to hydrolysis.

According to the invention, this object is achieved by the fact that the drug form itself contains a water-binding component. This water-binding component of the drug form in the transdermal therapeutic system binds moisture which has entered through the primary package, which moisture does not lead to the hydrolysis of the hydrolysis-sensitive active ingredient in the system. This applies in particular to moisture having entered through the primary package during storage, for example due to unfavorable storage conditions.

DETAILED DESCRIPTION OF THE INVENTION

The manner of incorporation into the drug form and the degree of dispersion are of no significance for the function of binding moisture for protection against hydrolysis. For the use of a substance as water-binding ingredient, the state of aggregation of the substance before and after the incorporation is likewise of no significance, as long as the water-binding function is maintained.

In simple semi-solid preparations, such as ointments, pastes or non-aqueous gels, for example, this can be achieved by incorporation of the water-binding components for example by dispersion in the liquid or semi-solid starting materials.

In patch-like transdermal systems the water-binding ingredient can be incorporated in the active substance reservoir itself or in other adhesive or reservoir layers or controlling membranes located in front of or behind the active substance reservoir.

Since in the production of transdermal therapeutic systems comprising a hydrolysis-sensitive component, water is largely excluded, it is easily possible to integrate the incorporation of the water-binding substance in such a system into the production process.

The system may have several layers, and at least one layer may contain a water-binding component. The water-binding component may be of mineral or non-mineral nature.

One embodiment further provides for the matrix or one of its layers to contain an acrylic-acid ester copolymer, a polyisobutylene, an ethylene-vinyl-acetate polymer, or styrene-isoprene block polymer, or a synthetic isoprene-isobutylene copolymer, or a hot-melt adhesive.

For example, the active substance may be acetyl salicylic acid and be present in the matrix in dissolved or dispersed form.

Further, the active substance may be bopindolol and be present in the matrix in dissolved or dispersed form.

Advantageously, the water-binding component portion of the entire matrix material amounts to at least 1%-wt., preferably up to 30%-wt. more preferably between 5 and 30%-wt.

A further embodiment provides that the mineral water-binding portion is the anhydrate (i.e. the water-free form) of an earth alkaline metal salt or alkali metal salt.

In the above case, the mineral water-binding component may be the semihydrate or the anhydrate of calcium sulfate.

It is of advantage if the matrix material contains the water-binding ingredient in finely dispersed suspension.

Besides, the active substance may be present as a dispersion of a water-free crystallisate.

A further essential measure provides that the transdermal therapeutic system is arranged in a pack in a gastight sealed means of packaging or package and that the means of packaging or package is rendered sufficiently water vapour resistant to maintain the water-binding capacity of the water-binding additive over the storage period. In addition, the package or means of packaging may contain a drying agent.

The transdermal therapeutic system can be in the form of a patch which comprises a suitable backing layer, and an active substance reservoir connected to the backing layer. In the absence of another control mechanism, a membrane controlling the release of the active substance is used. Also included is a pressure-sensitive adhesive device for affixing the system of on the skin, and, if required, a protective layer which is removable prior to application of the system. The active substance reservoir may contain oleogel.

In the following the invention will be further illustrated by means of examples.

EXAMPLE 1

Individually Dosed Acetylsalicylic Acid-Comprising Oleogel

A homogeneous mixture of 26 g acetylsalicylic acid (finely pulverised) and 10 g micronized calcium sulfate are dispersed, while stirring, in 26 g Miglyol®812. The resultant dispersion is converted into an oily gel-like dispersion by successive addition of up to 7 g hydrophobic, colloidal silicic acid. The dispersion is immediately dosed into suitable flat bags, the flat bag being subsequently sealed gastight.

EXAMPLE 2

Acetylsalicylic Acid-Containing Transdermal Therapeutic System 10 g acetylsalicylic acid (finely pulverised) and 15 g micronised calcium sulfate are processed to yield a homogeneous powder mixture, which is subsequently worked into 200 g solvent-containing polyacrylate while stirring. The resultant suspension is spread onto a siliconised polyethylene film with a 300 µm doctor knife, and the solvents are removed by drying for 20 minutes at 80° C. The adhesive film is covered with a polyester film. The so-obtained compound is cut to the required size with the aid of cutting tools, and is introduced in the primary package or means of packaging in a largely water-free atmosphere and welded so as to be gastight.

We claim:

1. A transdermal therapeutic system (TTS) comprising an active substance which is sensitive to hydrolysis and having a layered structure comprising a backing layer impermeable to moisture and the active substance, a matrix comprising the active substance and optionally a protective layer covering the matrix, wherein said matrix further comprises a water-binding component which is a mineral substance stabilizing said active substance against hydrolysis during storage.

2. The transdermal therapeutic system according to claim 1, wherein said matrix comprises several layers, wherein at least one layer contains said water-binding component.

3. The transdermal therapeutic system according to claim 1, wherein said matrix comprises an acrylic acid ester copolymer, a polyisobutylene, an ethylene-vinyl-acetate polymer, or styrene-isoprene block polymer, or a synthetic isoprene-isobutylene copolymer, or a hot-melt adhesive.

4. The transdermal therapeutic system according to claim 2, wherein one of said layers of said matrix comprises an acrylic acid ester copolymer, a polyisobutylene, an ethylene-vinyl-acetate polymer, or styrene-isoprene block polymer, or a synthetic isoprene-isobutylene copolymer, or a hot-melt adhesive.

5. The transdermal therapeutic system according to claim 1 wherein said active substance is acetylsalicylic acid, and is present in the matrix in a dissolved or dispersed form.

6. The transdermal therapeutic system according to claim 1, wherein said active substance is bopindolol, and is present in the matrix in a dissolved or dispersed form.

7. The transdermal therapeutic system according to claim 1, wherein the portion of said water-binding component in the entire matrix material is at least 1%-wt.

8. The transdermal therapeutic system according to claim 7, wherein the portion of said water binding component is 5 to 30%-wt.

9. The transdermal therapeutic system according to claim 1, wherein said mineral water-binding substance is the anhydrate of an earth alkaline metal salt or alkali metal salt.

10. The transdermal therapeutic system according to claim 9, wherein said mineral water-binding component is the semihydrate or the anhydrate of calcium sulfate.

11. The transdermal therapeutic system according to claim 1, wherein the matrix material of said matrix contains the water-binding component as a finely dispersed suspension.

12. The transdermal therapeutic system according to claim 1, wherein said active substance is present as a dispersion of a water-free crystallizate.

13. The transdermal therapeutic system according to claim 1, wherein said system is present in the form of a semi-solid preparation.

14. The transdermal therapeutic system according claim 1, wherein said system is present in the form of a patch and comprises said backing layer, an active substance reservoir connected to said backing layer as said matrix, in the absence of other control mechanisms, a membrane controlling the release of said active substance, a pressure-sensitive adhesive device for affixing said system to the skin, and, if required, a protective layer which is removable prior to application of the system.

15. The transdermal therapeutic system according to claim 2, comprising at least one polymer matrix layer.

16. The transdermal therapeutic system according to claim 15, wherein said at least one polymer matrix layer comprises an acrylic acid copolymer.

17. The transdermal therapeutic system according to claim 14, wherein said active substance reservoir is present in a liquid or semi-solid phase.

18. The transdermal therapeutic system according to claim 14, wherein said active substance reservoir contains an oleogel.

19. The transdermal therapeutic system (TTS) comprising an active substance which is sensitive to hydrolysis and having a layered structure comprising a backing layer impermeable to moisture and the active substance, a matrix comprising the active substance and a water-binding component stabilizing said active substance against hydrolysis during storage, optionally a protective layer covering the matrix, and a gas-tight sealed packing, sufficiently obstructing water vapor to maintain water-binding capacity of the water-binding additive over long storage periods.

20. The transdermal therapeutic system according to claim 19, wherein said packing additionally contains a drying agent.

\* \* \* \* \*